United States Patent [19]

Scherowsky et al.

[11] Patent Number: 5,336,436
[45] Date of Patent: Aug. 9, 1994

[54] OPTICALLY ACTIVE OXIRANE DERIVATIVES, AND THEIR USE AS DOPES IN LIQUID-CRYSTAL MIXTURES

[75] Inventors: Günter Scherowsky; Kirsten Grüneberg, both of Berlin, Fed. Rep. of Germany

[73] Assignee: Hoechst Aktiengesellschaft, Frankfurt am Main, Fed. Rep. of Germany

[21] Appl. No.: 902,990

[22] Filed: Jun. 22, 1992

[30] Foreign Application Priority Data

Jun. 24, 1991 [DE] Fed. Rep. of Germany ....... 4120783

[51] Int. Cl.$^5$ .................. C09K 19/34; C07D 239/02; C07D 303/12
[52] U.S. Cl. .................. 252/299.61; 252/299.64; 252/299.65; 252/299.66; 252/299.67; 544/298; 544/335; 526/268; 548/136; 549/60; 549/512; 549/555; 549/556; 549/557; 549/560
[58] Field of Search ............. 252/299.01, 299.61, 252/299.64, 299.65, 299.66, 299.67; 544/298, 335; 526/268; 548/136; 549/60, 512, 551, 554, 555, 556, 557, 560; 359/103

[56] References Cited

U.S. PATENT DOCUMENTS

| | | | |
|---|---|---|---|
| 4,638,073 | 1/1987 | Walba et al. | 252/299.61 |
| 4,876,028 | 10/1989 | Hemmerling et al. | 252/299.61 |
| 4,927,244 | 5/1990 | Bahr et al. | 359/103 |
| 4,988,459 | 1/1991 | Scherowsky et al. | 252/299.61 |
| 4,997,591 | 3/1991 | Heppke et al. | 252/299.61 |
| 5,167,855 | 12/1992 | Wand et al. | 252/299.01 |

FOREIGN PATENT DOCUMENTS 292954 11/1988 European Pat. Off. .

OTHER PUBLICATIONS

Ferroelectric Liquid Crystals Principles, Properties and Applications, G. W. Taylor, Ed., Gordon and Breach Science Publishers (Philadelphia), pp. 133–140 (1991).

*Primary Examiner*—Shean Wu
*Attorney, Agent, or Firm*—Curtis, Morris & Safford

[57] ABSTRACT

Optically active oxirane derivatives containing a mesogenic molecular unit are suitable as dopes in liquid-crystal mixtures. They give liquid-crystalline ferroelectric phases having short response times and electroclinic phases having large electroclinic coefficients. A further advantage is that they induce a helix of very small pitch, so that they are also suitable for helix compensation in LC mixtures.

6 Claims, No Drawings

OPTICALLY ACTIVE OXIRANE DERIVATIVES, AND THEIR USE AS DOPES IN LIQUID-CRYSTAL MIXTURES

In particular in the last decade, liquid crystals have found their way into various industrial areas in which electro-optical and display-device properties are demanded (for example in watch, calculator and typewriter displays). These display devices are based on dielectric alignment effects in the nematic, cholesteric and/or smectic phases of the liquid-crystalline compounds, where —as a result of the dielectric anisotropy—the molecular long axis of the compounds adopts a preferential alignment in an applied electrical field. The conventional response times in these display devices are rather too long for many other potential areas of application of liquid crystals, which are very promising chemical compounds for industry due to their unique properties. This disadvantage is particularly apparent if a large number of pixels must be addressed, which raises excessively the production costs of instruments containing relatively large areas, for example video equipment, oscillographs or TV, radar, EDP or word processor screens.

In addition to nematic and cholesteric liquid crystals, optically active smectic liquid-crystal phases have also become increasingly important in the last few years.

Clark and Lagerwall were able to show that the use of ferroelectric liquid-crystal systems in very thin cells results in electro-optical switching or display elements which, compared with conventional TN ("twisted nematic") cells, have response times which are faster by a factor of up to 1000 (cf., for example, Lagerwall et al., "Ferroelectric Liquid Crystals for Displays", SID Symposium, October Meeting, 1985, San Diego, Calif., USA). Due to these and other favorable properties, for example the possibility of bistable switching and the contrast which is virtually independent of the viewing angle, FLCs are in principle highly suitable for the abovementioned areas of application, for example via matrix addressing.

Another electro-optical effect, known as the electroclinic effect, is exhibited by orthogonal chiral smectic phases, for example $S^*_A$, $S^*_B$ and $S^*_E$. This effect [S. Garoff and R. B. Meyer, Phys. Rev. Lett. 38, 848 (1977)] comprises a field-induced tilt of the molecules, whose tilt angle $\phi$ changes proportionally to the applied field. The molecules of the orthogonal phases can follow, in particular, an alternating field to a limiting frequency $f_1$, while ferroelectric systems change their tilt angle suddenly each time a certain field strength is reached and retain this angle until a corresponding field of the opposite direction is applied (bistable switching).

The two effects, ferroelectric and electroclinic, can be utilized, depending on their specific properties, for the construction of electro-optical switching and display elements. This requires either compounds which form tilted or orthogonal smectic phases and are themselves optically active, or ferroelectric or electroclinic smectic phases can be induced by doping compounds which, although themselves forming smectic phases of this type, are not themselves optically active, with optically active compounds. The desired phase should be stable over the broadest possible temperature range.

In order to achieve good contrast in electro-optical components, a uniform planar alignment of liquid crystals is necessary. Good alignment in the $S^*_A$ and $S^*_C$ phases can be achieved if the phase sequence of the liquid-crystal mixture is, with decreasing temperature:

isotropic→N*→$S^*_A$→$S^*_C$.

The prerequisite is that the pitch of the helix in the N* phase is very large (greater than 10 μm) or even better is fully compensated (T. Matsumoto et al., p. 468–470, Proc. of the 6th Int. Display Research Conf., Japan Display, Sept. 30–Oct. 2, 1986, Tokyo, Japan; M. Murakami et al., ibid., p. 344–p. 347). This is achieved by adding to the chiral liquid-crystal mixture which has, for example, a left-handed helix in the N* phase, a further optically active dope which induces a right-handed helix, in such amounts that the helix is just compensated.

It has been described (EP 0 292 954) that optically active oxirane-2-carboxylic acid esters as dopes result in short response times in tilted smectic liquid-crystal phases, even when added in small amounts, and in high electroclinic coefficients in orthogonal smectic liquid-crystal phases. It is particularly surprising here that the pitch of the helix induced in the N* phase by doping is so small that even very small amounts added to a twisted phase having the opposite direction of rotation can compensate its twist.

The invention relates to novel optically active oxirane derivatives as dopes in liquid-crystal systems. The invention furthermore relates to liquid-crystal systems which contain these optically active oxirane derivatives. The oxirane derivatives to be employed according to the invention conform to the formula (I)

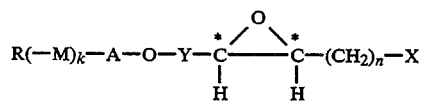

in which:
R is a straight-chain or branched alkyl or alkenyl radical having 6 to 12 carbon atoms and possibly containing an asymmetrical carbon atom,
—M is —O, —S, —O—CO, —CO—O or —CO,
—A is a radical of the subformulae below, in which the phenylene ring may also be monosubstituted or disubstituted by F

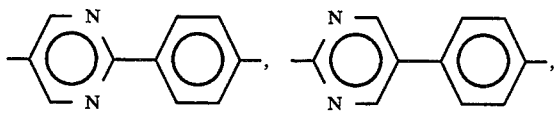

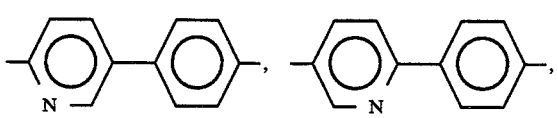

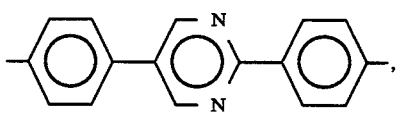

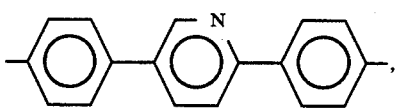

-continued

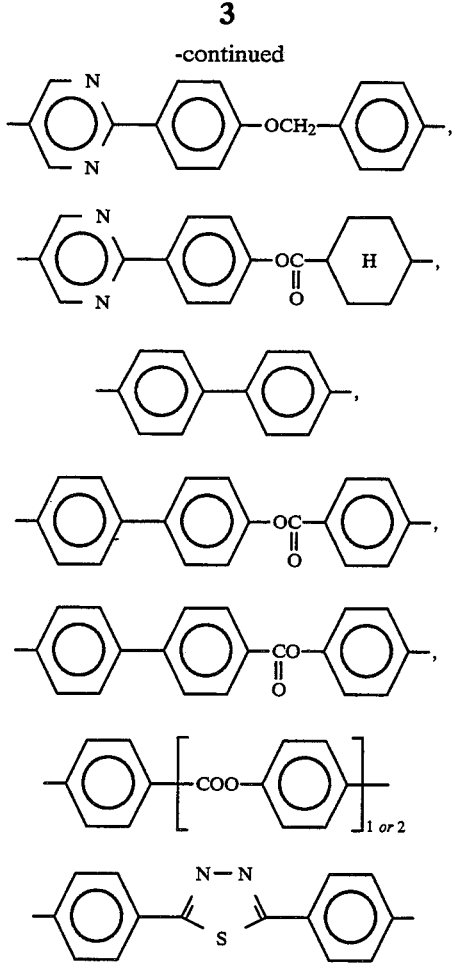

X is H₃COCH₂CH₂OCH₂O—, alkoxy, alkylcarbonyloxy, halogen, trialkylsilyloxy or tetrahydropyranyloxy,
Y is —CH₂— or —CO—,
n is 1 to 10, and
k is 0 or 1.

Particular preference is given to the compound of the formula below:

J. Org. Chem. 46, 3936 (1981); Djerassi et al., J. Am. Chem. Soc. 105, 2408 (1983).

The liquid-crystal mixtures according to the invention form liquid-crystal phases and contain at least one optically active oxirane derivative of the formula I.

The term "liquid-crystal phase" is taken to mean nematic, cholesteric, orthogonal smectic or tilted smectic phases, in particular S*$_A$, S*$_B$ and S*$_C$ phases. The liquid-crystal mixtures comprise 2 to 20, preferably 2 to 15, components, including at least one of the chiral compounds claimed according to the invention.

The other constituents are preferably selected from known compounds having nematic, cholesteric and/or smectic phases, for example S$_A$ phases, and/or tilted smectic phases; these include, for example, Schiff's bases, biphenyls, terphenyls, phenylcyclohexanes, cyclohexylbiphenyls, N-, S- or O-containing heterocyclic compounds (for example pyrimidines), cinnamic acid esters, cholesterol esters, various bridged, polycyclic esters of p-alkylbenzoic acids with terminal polar groups. In general, the commercially available liquid-crystal mixtures, even before addition of the optically active compound(s), are in the form of mixtures or a variety of components, of which at least one is a mesogenic, ie. as a compound which, in derivatized form or mixed with certain cocomponents, has a liquid-crystal phase which gives rise to expectations of formation of at least one enantiotropic (clearing point > melting point) or monotropic (clearing point < melting point) mesophase.

In particular, the liquid-crystal mixture, in addition to at least one of the optically active compounds claimed according to the invention, contains an ester compound having a S$_C$ phase, for example a phenyl alkoxybenzoate, or a biaromatic compound containing a nitrogen-containing heterocyclic ring, for example an alkylpyrimidinylalkoxybenzene.

The liquid-crystal mixtures generally contain from 0.05 to 70% by weight, in particular from 0.1 to 50% by weight, of the compound(s) according to the invention.

The compounds according to the invention are particularly suitable as dopes for tilted smectic liquid-crystal phases, since they convert the latter into ferroelectric liquid-crystal phases; the values for the spontaneous

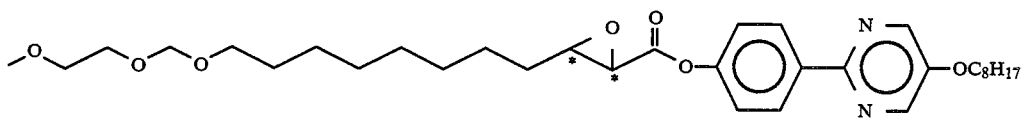

To prepare the compounds of the formula (I), mesogenic phenols of the formula (II)

R(—M)—A—OH (II)

are reacted with derivatives of the formula (III)

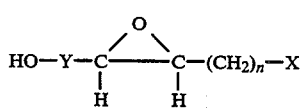

where the symbols are as defined above. Phenols of the formula (II) are known. The methods for the preparation of the oxirane derivatives (III) according to the invention are also known, for example Sharpless et al., polarization (P$_s$) for 10 mol% doping and at 25° C. are in the range from about 1–15 nC/cm², and in the range of about 10–150 nC/cm², extrapolated linearly to the pure compound, and in some cases the values for P$_s$ are even higher.

The response times of the novel systems are frequently less than 100 μs at 10 mol% doping, 25° C. and a switching voltage of ±10 V/μm. The compounds according to the invention can also be employed to achieve the electroclinic effect in orthogonal smectic phases (S*$_A$, S*$_B$ and S*$_E$). The invention is described in greater detail in the Examples below.

Example 1

9-(Methoxyethoxymethoxy)nonanol 1

1.1 mmol of 1,9-nonanediol are dissolved in absolute THF in a two-neck flask which has been flee-treated and flushed with nitrogen. 1.1mmol of absolute triethylamine and 1 mmol of MEM chloride are added dropwise with stirring at 0° C. The mixture is stirred at 0° C. for 2 hours and at room temperature overnight. Triethylammonium chloride is filtered off, and the solution is evaporated on a rotary evaporator. The yellowish, oily crude product obtained is purified by flash chromatography (PE/$CH_2Cl_2$).

| Batch: | |
| --- | --- |
| 6.5 g (0.0406 mol) | of 1,9-nonanediol |
| 4.1 g (0.0406 mol) | of $NEt_3$ (abs.) |
| 4.6 g (0.037 mol) | of MEM (methoxyethoxymethoxy) chloride |
| 50 ml | of THF (abs.) |
| Yield: 3.68 g (40%) | |
| $C_{15}H_{26}O$: (248.35) | |

Example 2

9-(Methoxyethoxymethoxy)nonanal 2

About 5 ml of the solvent mixture benzene/DMSO (1:1) are introduced into a two-neck flask which has been flame-treated and flushed with nitrogen, and 1 mmol of absolute pyridine and 0.5 mmol of $CF_3COOH$, and 1 mmol of 1 and 3 mmol of dicyclohexylcarbodiimide (DCCI), dissolved in benzene/DMSO, are added with stirring. The mixture is stirred overnight at room temperature. Precipitated dicyclohexylurea is filtered off, and the solution is evaporated on a rotary evaporator. DMSO is removed by repeated shaking with water and, if necessary, at 40° C. in a bulb tube. The crude product is filtered again and purified by flash chromatography (PE/$CH_2Cl_2$).

| Batch: | |
| --- | --- |
| 3.68 g (14.8 mmol) | of 1 |
| 9.95 g (48.2 mmol) | of DCCI |
| 1.17 g (14.8 mmol) | of pyridine (abs.) |
| 0.56 g (7.4 mmol) | of $CF_3COOH$ |
| 50 ml | of benzene (abs.)/DMSO (abs.) (1:1) |
| Yield: 3.57 g (98%) | |
| $C_{13}H_{26}O_4$ (246.334) | |

Example 3

Ethyl (E)-11-(methoxyethoxymethoxy)-2-undecenoate 3

1 mmol of 2 and 1 mmol of diethyl (ethoxycarbonyl)methyl phosphonate are introduced into a two-neck flask which has been flame-treated and flushed with nitrogen, and sodium methanolate is slowly added dropwise. The reaction solution is stirred overnight at room temperature and evaporated on a rotary evaporator. The residue is taken up in ether, the solution is washed three times with water and saturated NaCl solution, the organic phase is dried over $MgSO_4$, and the solvent is removed in vacuo. The product is purified by flash chromatography (PE/$CH_2Cl_2$)

| Batch: | |
| --- | --- |
| 3.46 g (14 mmol) | of 2 |
| 3.33 g (14 mmol) | of diethyl (ethoxycarbonyl)methyl phosphonate |
| 0.321 g | of Na |
| 7.13 ml | of methanol |
| 30 ml | of THF (abs.) |
| Yield: 2.5 g (56%) | |
| $C_{17}H_{32}O_5$ (316.421) | |

Example 4

(E)-11(methoxyethoxymethoxy)-2-undecen-1-ol 4

2 mmol of diisobutylaluminum hydride (DIBAH) (1.2 molar solution in toluene) are added with exclusion of moisture to a solution of 1 mmol of 3 in 20 ml of THF (abs.) at such a rate that the temperature does not exceed 40° C. The mixture is stirred at room temperature for 2 hours. Excess DIBAH is carefully hydrolyzed by means of methanol/$H_2O$, the mixture is stirred for 20 minutes, and ether is added. The precipitate is filtered off with suction and washed several times with ether. The solution is dried over $MgSO_4$, and the solvent is removed in vacuo. The product is purified by flash chromatography (PE/$CH_2Cl_2$)

| Batch: | |
| --- | --- |
| 1.52 g (4.8 mmol) | of 3 |
| 8 ml | of DIBAH solution (c = 1.2 mol/l in toluene) |
| 30 ml | of THF (abs.) |
| Yield: 1.2 g (91%) | |
| $C_{15}H_{30}O_4$ (274.386) | |

Example 5

(2S,3S)-(-)-3-[8-(methoxyethoxymethoxy)octyl]-2-hydroxymethyloxirane 5

200 ml of absolute $CH_2Cl_2$ are cooled to between $-25°$ C. and $-30°$ C. (dry ice/methanol) in a three-neck flask which has been dried by heating and flushed with nitrogen. 20 mmol of tetraisopropyl titanate [Ti(O—i—$C_3H_7$)$_4$] and 20 mmol of L-(+)-diethyl tartrate (L-(+)-DET), dissolved in 2 ml of absolute $CH_2Cl_2$, are added with stirring through a septum. After 5 to 10 minutes, 20 mmol of the allyl alcohol 4 are added, dissolved in a little absolute $CH_2Cl_2$, and finally 40 mmol of a 3.0 molar solution of tert.butyl hydroperoxide (TBHP) in toluene are added. The resultant solution is left to stand overnight at $-25°$ C. 50 ml of a 10% strength solution of tartaric acid in water are then added with stirring at $-25°$ C. After 30 minutes, the cooling bath is removed, and stirring is continued at room temperature until the aqueous solution separates out and is clear. The phases are separated, the organic phase is washed once with water, and the solvent is removed on a rotary evaporator. The residue is taken up in 150 ml of $Et_2O$, and 60 ml of a precooled 1N NaOH solution are added to the resultant solution at 0° C. The two-phase system is stirred at 0° C. for 30 minutes. The phases are then separated, the etherial phase is washed once with saturated NaCl solution and dried over $MgSO_4$, and the solvent is stripped off. The crude substance obtained is purified by flash chromatography.

| Batch: | | |
|---|---|---|
| 1.1 g | (4 mmol) | of 4 |
| 1.137 g | (4 mmol) | of Ti (O-i-prop)$_4$ |
| 825 mg | (4 mmol) | of L-(+)-DET |
| 8 ml | | of TBHP (c = 3 mol/l of toluene |
| 50 ml | | of CH$_2$Cl$_2$ (abs.) |
| Yield: 896 mg (77%) | | |
| ee > 95% | | |
| $[\alpha]_D^{25} = -15.2°$, c = 0.96 | | |
| C$_{13}$H$_{30}$O$_5$ (290.385) | | |

Example 6

(2R, 3S)-(-)-3-
[8-(methoxyethoxymethoxy)octyl]oxirane-2-carboxylic acid 6

2.5 ml of tetrachloromethane, 2.5 ml of acetonitrile, 3.9 ml of water, 1.5 mmol of the alcohol 5, 4.5 mmol of sodium periodate and 5 mol % of ruthenium(III) chloride trihydrate are combined in this sequence, and the mixture is stirred overnight at room temperature. The batch is evaporated, and the residue is taken up in 10 ml of saturated NaCl solution and 8 ml of CH$_2$Cl$_2$. The phases are separated, the aqueous phase is extracted with CH$_2$Cl$_2$, the combined organic phases are washed with saturated NaCl solution and dried over MgSO$_4$, and the solvent is removed in vacuo. The oxiranecarboxylic acid obtained is employed without further purification.

| Batch: | | |
|---|---|---|
| 688 mg | (2.387 mmol) | of 5 |
| 1.52 g | (7.11 mmol) | of NaIO$_4$ |
| 119 mg | (5 mol %) | of RuCl$_3$.3H$_2$O |
| 4 ml | | of CCl$_4$ |
| 4 ml | | of CH$_3$CN |
| 6 ml | | of H$_2$O |
| Yield: 692 mg (96%) | | |
| C$_{13}$H$_{26}$O$_6$ (304.368) | | |

Example 7

4-(5-octyloxypyrimidin-5-yl)phenyl (2R,3S)-(-)-3-[8-(methoxyethoxymethoxy)octyl]oxirane-2-carboxylate 1 mmol of the appropriate alcohol, 1 mmol of the carboxylic acid 6 and 0.1 mmol of 4-dimethylaminopyridine (DMAP) in 50 ml of absolute CH$_2$Cl$_2$ are introduced into a two-neck flask which has been flame-treated and flushed with nitrogen. 1 mmol of dicyclohexylcarbodiimide (DCCI) is added at 0° C., and the mixture is stirred at 0° C. for half an hour and at room temperature overnight. The precipitated urea is filtered off, the organic phase is washed once with saturated NaCl solution and dried over MgSO$_4$, and the solvent is removed on a rotary evaporator. The crude product is purified by flash chromatography (PE/CH$_2$Cl$_2$).

| Batch: | | |
|---|---|---|
| 692 mg | (2.27 mmol) | of 6 |
| 682 mg | (2.27 mmol) | of 2-(4-hydroxyphenyl)-5-octyloxy-pyrimidine |
| 469 mg | (2.27 mmol) | of DCCI |
| 28 mg | (0.227 mmol) | of DMAP |
| 50 ml | | of CH$_2$Cl$_2$ (abs.) |
| Yield: 600 mg (45%) | | |

-continued

| Batch: |
|---|
| $[\alpha]_D^{25} = -17.5°$, c = 1.03 |
| C$_{33}$H$_{50}$N$_2$O (586.737). |

We claim:
1. An oxirane derivative of the formula (I)

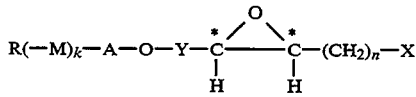

in which:
R is a straight-chain or branched alkyl or alkenyl radical having 6 to 12 carbon atoms and possibly containing an asymmetrical carbon atom;
M is —O, —S, —O—CO, —CO—O or —CO,
A is a radical of the subformulae below, in which the phenylene ring may also be monosubstituted or disubstituted by F

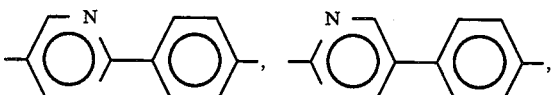

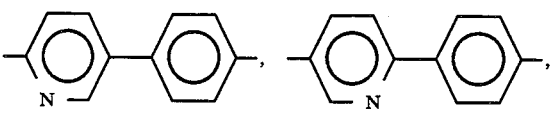

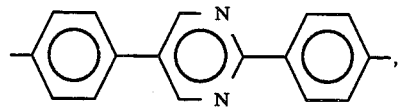

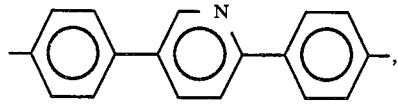

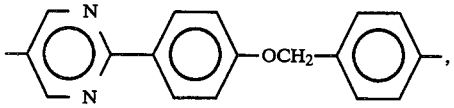

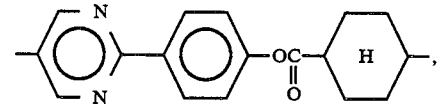

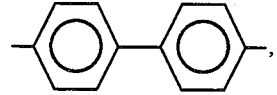

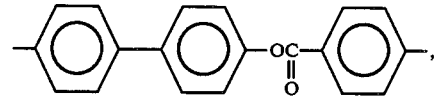

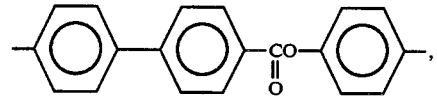

-continued

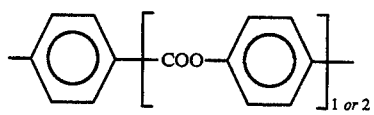

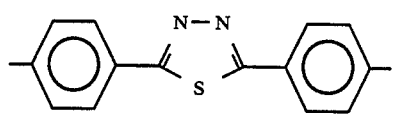

X is H₃COCH₂CH₂OCH₂O—, halogen, trialkylsilyloxy or tetrahydropyranyloxy,
Y is —CH₂— or —CO—,
n is 1 to 10, and
k is 0 or 1.

2. A liquid-crystal mixture containing an optically active oxirane derivative of the formula I as claimed in claim 1.

3. An electro-optical switching or display device containing a liquid-crystal mixture as claimed in claim 2.

4. An oxirane derivative of the formula (I)

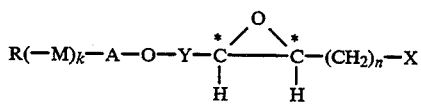

in which:

R is a straight-chain or branched alkyl or alkenyl radical having 6 to 12 carbon atoms and possible containing an asymmetrical carbon atom;

M is M is —O—, —S—, —O—CO—, —CO—O or —CO,

A is a radical of the subformulae below, in which the phenylene ring is monosubstituted or disubstituted by F

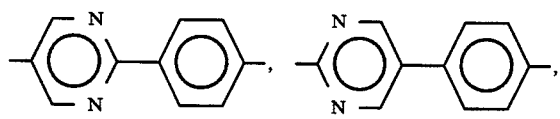

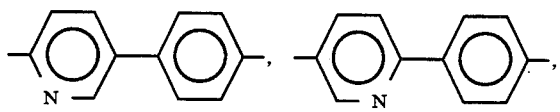

X is H₃COCH₂CH₂OCH₂O—, alkoxy, alkylcarbonyloxy, halogen, trialkylsilyloxy or tetrahydropyranyloxy,
Y is —CH₂— or —CO—,
n is 1 to 10, and
k is 0 or 1.

5. A liquid-crystal mixture containing an optically active oxirane derivative of the formula I as claimed in claim 4.

6. An electro-optical switching or display device containing a liquid-crystal mixture as claimed in claim 5.

* * * * *